United States Patent [19]

Bandurco et al.

[11] Patent Number: 4,490,374
[45] Date of Patent: Dec. 25, 1984

[54] 5,6-DIALKOXY-3,4-OPTIONALLY SUBSTITUTED-2(1H)QUINAZOLINONES, COMPOSITION AND METHOD OF USE

[75] Inventors: Victor T. Bandurco, Bridgewater; Seymour D. Levine, North Brunswick, both of N.J.; Dennis M. Mulvey, New Hope; Alfonso J. Tobia, Doylestown, both of Pa.

[73] Assignee: Ortho Pharmaceutical Corporation, Raritan, N.J.

[21] Appl. No.: 430,552

[22] Filed: Sep. 30, 1982

[51] Int. Cl.³ .................. A61K 31/505; C07D 239/80
[52] U.S. Cl. .................................... 424/251; 544/116; 544/118; 544/284; 544/286; 549/451; 549/452; 560/29; 568/425
[58] Field of Search .................. 544/286; 424/251

[56] References Cited

U.S. PATENT DOCUMENTS 3,859,237 1/1975 Inaba et al. .................. 424/251
3,950,526 4/1976 Inaba et al. .................. 424/251

FOREIGN PATENT DOCUMENTS 765947 10/1970 Belgium .
52-17842 2/1977 Japan .................. 544/286
7209078 1/1973 Netherlands .................. 544/286
2088874 6/1982 United Kingdom .

*Primary Examiner*—Glennon H. Hollrah
*Assistant Examiner*—James H. Turnipseed
*Attorney, Agent, or Firm*—Benjamin F. Lambert

[57] ABSTRACT

The synthesis of substituted quinazolinones is described. The novel quinazolinones are renal vasodilators and thereby increase renal blood flow, and are useful as cardiovascular agents.

6 Claims, No Drawings

5,6-DIALKOXY-3,4-OPTIONALLY SUBSTITUTED-2(1H)QUINAZOLINONES, COMPOSITION AND METHOD OF USE

The present invention relates to substituted quinazolinones having functionality at $N_1$. The substituted quinazolinones which are the subject of this invention have the following formula

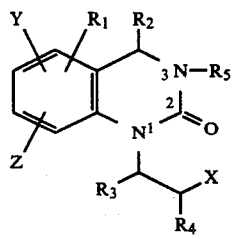

wherein $R_1$ is hydrogen, amino or nitro; $R_2$ is hydrogen, alkyl having 1–20 carbon atoms, cycloalkyl having 4–8 carbon atoms, cycloalkylalkyl wherein the cycloalkyl group has 4–8 carbon atoms and the alkyl group has 1–3 carbon atoms, haloalkyl having 1–3 halogen atoms and 1–4 carbon atoms and the halogen is chloro, bromo or fluoro, and bicycloalkyl such as norbornyl and norbornylmethyl; $R_3$ and $R_4$ may be the same or different and are hydrogen, lower alkyl having 1–6 carbon atoms, aryl and substituted aryl such as phenyl, 2-, 3-, and 4-pyridyl, o-, m-, and p-hydroxyphenyl, halophenyl such as p-chlorophenyl, p-fluorophenyl, o-chlorophenyl, 2,4-difluorophenyl, lower alkoxyphenyl such as methoxy, ethoxy, and butoxyphenyl, alkylphenyl wherein the alkyl group contains 1–6 carbon atoms; X is benzyl, carboxy, carboalkoxy wherein the alkoxy group has 1–3 carbon atoms, cyano, carboxamido, methanesulfonyl, formyl, aroyl, such as benzoyl, substituted benzoyl wherein the substituent is an alkyl group having 1–4 carbon atoms, heteroaryl such as 2-, 3-, and 4-pyridyl, and 2-thienyl; heteroaroyl, such as 2-, 3-, and 4-pyridoyl, 2-thienoyl, 2-furoyl and 3-(1,2,5) thiadiazolyl; $R_5$ is hydrogen, lower alkyl having 1–6 carbons; benzyl or substituted benzyl wherein the substituent is fluoro, chloro, bromo, alkyl or alkoxy wherein the alkyl group has 1–6 carbon atoms; provided that when $R_5$ is other than hydrogen the compound is a quaternary salt when the 3,4-imine linkage is unsaturated; (the presence of an unsaturated imine linkage between $N_3$ and $C_4$ is optional and $N_3$ may or may not be substituted); Y and Z are hydrogen or hydroxy, provided that at least one of Y and Z is hydroxy (when Y and Z are both hydroxy the hydroxyl groups are positioned adjacent to each other at either the 5,6- or the 6,7-position); and including the alkali metal and alkaline earth metal salts of the phenolic hydroxyls and the carboxy group at N-1 and selected amine salts such as the salts of meglumine, piperazine, N-methylpiperazine, morpholine and aliphatic amines having 1–5 carbon atoms; aminoalcohols such as ethanolamine, 2-amino-1,3-propanediol and bis(hydroxymethyl)methylamine; and amino acids such as arginine, lysine and ornithine.

The preferred compounds of the present invention are those wherein $R_1$ is hydrogen; $R_2$ is hydrogen, alkyl, cycloalkyl, bicycloalkyl and haloalkyl; $R_3$ and $R_4$ are hydrogen, lower alkyl, aryl and substituted aryl; X is carboxy, carboalkoxy, cyano, carboxamido and formyl; $R_5$ is hydrogen, lower alkyl, benzyl, substituted benzyl, provided that when $R_5$ is other than hydrogen the compound is a quaternary salt when the 3,4-imine linkage is unsaturated (the unsaturated imine linkage between $N_3$ and $C_4$ is optional and $N_3$ may or may not be substituted); Y and Z are hydrogen or hydroxy, provided that at least one of Y and Z is hydroxy; and including the alkali metal and alkaline earth metal salts of the phenolic hydroxyls and the carboxy group at $N_1$ and selected amine salts such as the salts of meglumine, piperazine, N-methylpiperazine, morpholine and aliphatic amines having 1–5 carbon atoms; aminoalcohols such as ethanolamine, 2-amino-1,3-propanediol and bis(hydroxymethyl)methylamine; and amino acids such as arginine, lysine and ornithine. When Y and Z are both hydroxy, the hydroxyl groups are positioned adjacent to each other and are located at either the 5,6- or the 6,7-position.

Several 6,7-dialkoxy-4-alkyl 2(1H)quinazolinones have been reported in the literature [Budesinsky et al., *Coll. Czech. Chem. Commun.*, 37, 2779 (1972); Belgian Pat. No. 765947 (1971)]. None of the reported substituted quinazolinones have hydroxy groups substituted on the benzene ring. In addition, the known quinazolinones are not similarly substituted at $N_1$.

The novel quinazolinones of this invention are renal vasodilators. As such they increase renal blood flow and are therefore useful as cardiovascular agents. In addition, some of the compounds and some of the intermediates used to prepare the novel quinazolinones possess cardiotonic activity.

The substituted quinazolinones can be synthesized according to the following schematic diagram.

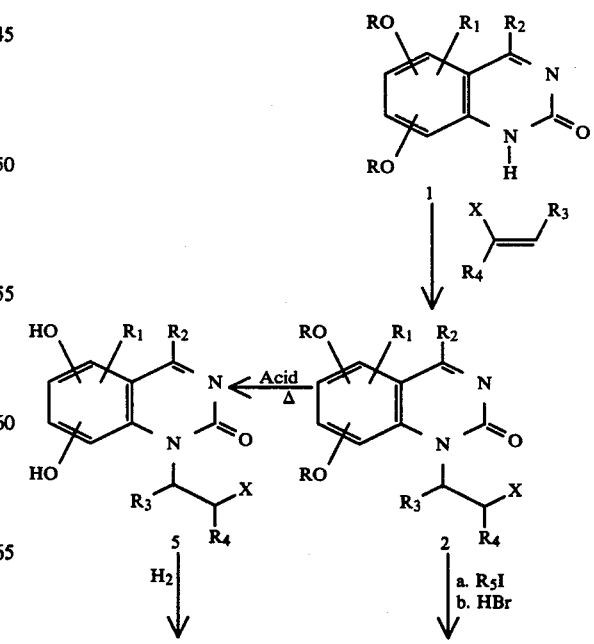

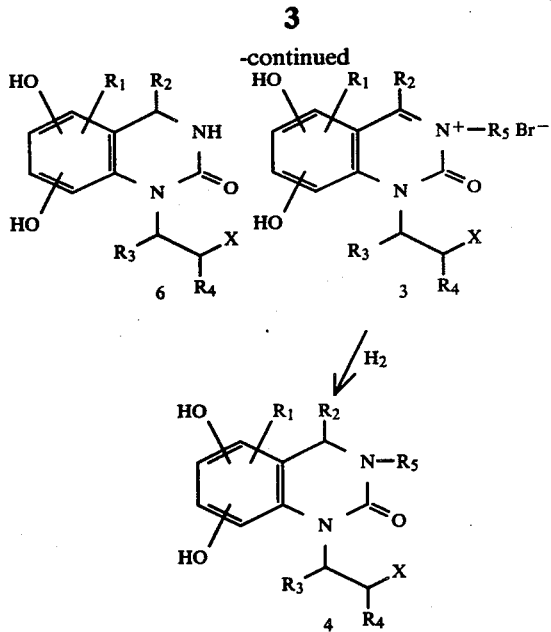

wherein $R_1$, $R_2$, $R_3$, $R_4$, $R_5$ and X are as defined above and R is lower alkyl having 1-5 carbon atoms.

As can be seen from the diagram, the $N_1$ substituted quinazolinone (2) is prepared by reacting a substituted quinazolinone with an appropriately substituted olefin, such as methyl cinnamate, methyl acrylate, methyl crotonate, acrylonitrile and methyl methacrylate, for example. The particular olefin employed will depend upon the type of substitution desired in the end product. The reaction is carried out in the presence of a basic catalyst such as sodium carbonate, potassium carbonate, potassium fluoride, sodium fluoride, potassium hydroxide, sodium hydroxide, alkali metal alkoxides such as potassium ethoxide, and sodium methoxide, quaternary ammonium hydroxides such as benzyltrimethylammonium hydroxide, quaternary ammonium fluorides such as tetraethylammonium fluoride and tertiary amines such as triethylamine. The reaction temperature employed can vary between $-10°$ C. and $100°$ C.; the preferred reaction temperature is about $65°$ C.

The $N_1$ substituted quinazolinone (2) can be used to prepare the other $N_1$ substituted quinazolinones by the routes shown in the diagram. For example, the $N_1$ substituted quinazolinone (2) can be conveniently alkylated with an alkyl iodide such as methyl or ethyl iodide or a benzyl iodide such as o-, m-, or p-fluorobenzyl, o-, m-, or p-methylbenzyl and o-, m-, or p-methoxybenzyl iodide to give the corresponding quaternary salt. The salt in turn can be hydrolyzed with an acid such as hydrobromic acid or hydriodic acid, for example, to give the corresponding dihydroxy compound (3). The $N_1$ substituted quinazolinone (2) can be converted directly to the corresponding dihydroxy compound (5) by reaction with an acid such as hydrobromic or hydriodic acid. The dihydroxy compounds (3 and 5) can then be partially saturated (4 and 6) by reaction with hydrogen in the presence of a catalyst such as platinum, palladium, rhodium or nickel. Ammonium formate, boranes and metallic hydrides such as sodium borohydride may also be employed as reagents in the reduction step.

The starting material (1) used in the preparation of the substituted hydroxyquinazolinones wherein the substituents on the benzene ring are in the 6,7-position can be prepared by two main routes. For the first, an appropriately substituted alkoxyaniline is converted to the corresponding isocyanate. The conversion is carried out with phosgene in a suitable solvent such as, for example, benzene, toluene or xylene. The isocyanate is then condensed with the appropriate carboxamide to form the corresponding adduct. The condensation can be carried out either neat or in an inert solvent such as xylene or toluene. It is preferred to carry out the reaction at a temperatue between $100°-150°$ C. The adduct is then cyclized to form a quinazolinone. Suitable cyclizing agents which can be employed include polyphosphoric acid, polyphosphoric ester and a mixture of phosphorous pentoxide and methanesulfonic acid. The ratio of the cyclizing agent to the adduct may vary between 1:1 and 25:1; however, the preferred ratio is 5:1. The reaction is preferably carried out at a temperature between $100°-130°$ C. in an inert atmosphere such as nitrogen. In the second route, an appropriately substituted acetophenone is nitrated. After separation of the isomers the substituted o-nitroacetophenone is reduced to the corresponding amine. This is turn is acylated with an alkylhaloformate to give the corresponding urethane. Cyclization of the urethane so obtained with ammonia gives the corresponding quinazolinone. Examples of these transformations are illustrated below.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain, dosage unit, e.g., tablet, capsule, powder, injection, teaspoonful and the like, from about 15 to about 300 mg/kg and preferably from about 30 to about 200 mg/kg of the active ingredient.

The following examples describe the invention in greater particularity and are intended to be a way of illustrating but not limiting the invention.

EXAMPLE 1

6,7-Dihydroxy-4-methyl-2(1H)quinazolinone-1-(3'-methyl)propionic acid Monohydrobromide Monohydrate A solution of methyl 6,7-dimethoxy-4-methyl-2(1H)quinazolinone-1-(3'-methyl)propionate (1.0 g, 3.2 mM) in acetic acid (10 ml) and 48% aqueous hydrogen bromide (10 ml) is refluxed for 66 hours. The reaction mixture is cooled. A green precipitate results which is isolated by filtration, washed with cold ether (20 ml) and dried under vacuum to afford the product (300 mg, 25%). mp 220°-222° C.; $\delta_{TMS}^{TFA}$ 1.71-1.95 (d, 3H, 3'—CH$_3$), 3.04 (s, 3H, 4—CH$_3$) 3.18-3.53 (m, 1H,

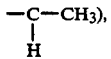

5.21-5.82 (m, 2H, —CH$_2$—), 7.62 (s, 1H, C$_5$—H), 7.79 (s, 1H, C$_8$—H); M+ 278.

EXAMPLE 2

6,7-Dihydroxy-3,4-dimethyl-2(1H)quinazolinonium-1-propionic acid Bromide

A solution of methyl 6,7-dimethoxy-3,4-dimethyl-2(1H)quinazolinonium-1-propionate iodide (1.5 g, 33 mM) in acetic acid (10.5 ml) and 48% aqueous hydrobromic acid (10.5 ml) is refluxed with stirring for 48 hours. The brown reaction mixture is cooled to room temperature and a yellow precipitate is isolated by filtration. After washing with cold ether (25 ml) and drying under vacuum, the product (650 mg, 55%) is isolated. mp 270°-272° C.; $\delta_{TMS}^{TFA}$ 3.22 (s, 3H, 4—CH$_3$), 3.01-3.42 (m, 2H, 2'—CH$_2$), 4.12 (s, 3H,

4.67-5.11 (t, 2H, 2'=CH$_2$), 7.47 (s, 1H, C$_5$—H), 7.93 (s, 1H, C$_8$—H); M+ 278 (M-80).

EXAMPLE 3

6,7-Dihydroxy-4-methyl-2(1H)quinazolinone-1-(2'-methyl)propionic acid

A solution of methyl 6,7-dimethoxy-4-methyl-2(1H)quinazolinone-1-(2'-methyl)propionate (2.40 g, 7.5 mM), acetic acid (25 ml) and 48% aqueous hydrogen bromide (25 ml) is refluxed for 48 hours under nitrogen. The reaction mixture is cooled in an ice bath, concentrated in vacuo to half volume and basified to pH 12 with 1N sodium hydroxide (25 ml). The reaction is chilled again and acidified with glacial acetic acid to pH 5. A yellow precipitate results which is isolated by filtration, washed with cold ether and dried under vacuum to afford the product. (1.60 g, 76.9%); mp 266°-268° C.; $\delta_{TMS}^{TFA}$ 1.38-1.65 (d, 3H, 2'—CH$_3$), 2.99 (s, 3H-4—CH$_3$), 3.10-3.49 (m, 1H,

3.91-5.09 (m, 2H,

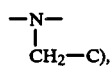

7.37 (s, 1H, C$_5$—H), 7.72 (s, 1H, C$_8$—H); M+ 278.

When in the above procedure methyl 6-methoxy-4-methyl-2(1H)quinazolinone-1-propionate, methyl 7-methoxy-4-methyl-2(1H)quinazolinone-1-propionate, methyl 6-methoxy-2(1H)quinazolinone-1-propionate, methyl 7-methoxy-2(1H)-quinazolinone-1-propionate, methyl 6-methoxy-4-trifluoromethyl-2(1H)quinazolinone-1-propionate and methyl 7-methoxy-4-trifluoromethyl-2(1H)quinazolinone-1-propionate are employed in place of methyl 6,7-dimethoxy-4-methyl-2(1H)quinazolinone-1-(2'-methyl)propionate the corresponding 6-hydroxy-4-methyl-2(1H)quinazolinone-1-propionic acid, 7-hydroxy-4-methyl-2(1H)quinazolinone-1-propionic acid, 6-hydroxy-2(1H)quinazolinone-1-propionic acid, 7-hydroxy-2(1H)quinazolinone-1-propionate, 6-hydroxy-4-trifluoromethyl-2(1H)quinazolinone-1-propionic acid and 7-hydroxy-4-trifluoromethyl-2(1H)quinazolinone-1-propionic acid are obtained.

EXAMPLE 4

6,7-Dihydroxy-4-methyl-2(1H)quinazolinone-1-(2'-methyl)propionic acid tripotassium salt monohydrate A suspension of 6,7-dihydroxy-4-methyl-2(1H)quinazolinone-1-(2'-methyl)propionic acid (1.5 g, 5.39 mM) in methanol (100 ml) is treated with 1.0N methanolic KOH (16.17 ml, 16.1 mM) with good stirring under nitrogen. The resulting dark solution is filtered under nitrogen and concentrated in vacuo to a yellow solid. The solid is triturated with acetone (40 ml) and isolated by filtration. After washing with ether (20 ml), the solid is dried in a dessicator under vacuum for 16 hours at room temperature to afford 6,7-dihydroxy-4-methyl-2(1H)quinazolinone-1-(2'-methyl)propionic acid tripotassium salt monohydrate (2.2 g, 100%); mp >300° C.

EXAMPLE 5

6,7-Dihydroxy-4-methyl-1-(3'-phenylpropyl)-2(1H)quinazolinone Monohydrate

A mixture of 6,7-dimethoxy-4-methyl-1-(3'-phenylpropyl)-2(1H)quinazolinone (1.25 g, 3.6 mM) and 48% aqueous hydrogen bromide (10 ml) in glacial acetic acid (10 ml) is refluxed with stirring for 24 hours. After cooling to room temperature, the reaction mixture is quenched on ice (100 g). A yellow-brown solid deposits which is isolated, washed with water (2×20 ml) and then with ether (3×40 ml). After drying in air, 1.21 g (100%) of the product is obtained. mp >275° C. dec.; $\delta_{TMS}^{TFA}$ 2.00-2.70 (m, 2H, —CH$_2$—), 2.75-3.30 (m, 2H, —CH$_2$—$\phi$), 3.00 (s, 3H, CH$_3$), 4.30-5.00 (t, 2H, —CH$_2$N), 7.07 and 7.65 (2s, 2H, C$_5$H, C$_8$H), 7.25 (s, 5H,$\phi$—); M+ 310.

When in the above procedure 6,7-dimethoxy-4-methyl-2(1H)quinazolinone-1-(2-methanesulfonyl)ethane, 6,7-dimethoxy-4-methyl-2(1H)quinazolinone-1-(2-benzoyl)ethane, and 6,7-dimethoxy-4-methyl-2(1H)quinazolinone-1-2-(2'-pyridyl)ethane, are employed in place of 6,7-dimethoxy-4-methyl-1-(3-phenylpropyl)-2(1H)quinazolinone the corresponding 6,7-dihydroxy-4-methyl-1-(2-methanesulfonyl)ethane-2(1H)quinazolinone monohydrate, 6,7-dihydroxy-4-methyl-1-2(benzoyl)ethane-2(1H)quinazolinone monohydrate, and 6,7-dihydroxy-4-methyl-1-2(2'-pyridyl)ethane-2(1H)quinazolinone monohydrate are obtained.

When in the above procedure 6,7-dimethoxy-4-methyl-2(1H)quinazolinone-1-propionaldehyde, 6,7-dimethoxy-4-methyl-2(1H)quinazolinone-1-propionitrile and methyl 6,7-dimethoxy-4-methyl-2(1H)quinazolinone-1-(1-phenyl)propionate are employed in place of 6,7-dimethoxy-4-methyl-1-(3-phenylpropyl)-2(1H)quinazolinone the corresponding 6,7-dihydroxy- 4-methyl-2(1H)quinazolinone-1-propionaldehyde, 6,7-dihydroxy-4-methyl-2(1H)quinazolinone-1-propionic acid and 6,7-dihydroxy-4-methyl-2(1H)quinazolinone-1-(1-phenyl)propionic acid are obtained.

The following compounds are prepared by the procedure of Examples 3, 4 or 5 using an appropriately substituted quinazolinone as the starting material.

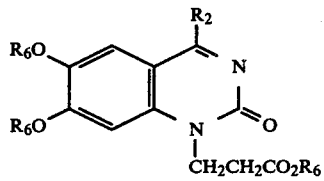

wherein $R_6$ is potassium or hydrogen and $R_2$ is as defined.

| $R_2$ | Hydrobromide Salt mp/Yield % | Free Acid mp/Yield % | Tripotassium Salt mp/Yield % |
|---|---|---|---|
| H | 231–232° C./57.8 | | |
| CH$_3$ | 257–259° C./82.5 | | >300° C./96.9 |
| CF$_3$ | | 125–130° C./22.2 | >310° C./76.6 |
| ethyl | | 308–310° C./84.5 | 305–306° C./73.8 |
| propyl | 264–266° C./42.8 | 328–329° C./71.4 | 310–312° C/.97.2 |
| isopropyl | | 310–312° C./73.3 | Dec. >300° C./74.0 |
| n-pentyl | 222–224° C./79.2 | 275–277° C./72.3 | |
| n-hexyl | | 242–246° C./64.3 | Dec. 220° C./68.2 |
| n-heptyl | | 248–250° C./91.6 | |
| n-octyl | | 238–240° C./55.1 | 302–304° C./80.0 |
| n-decyl | | 164–166° C./71.6 | 259–261° C./100.0 |
| CH$_2$—CH$_2$<br>\|    \|<br>CH$_2$—CH— | 276–278° C./88.0 | 228–230° C./8.9 | |
| CH$_2$—CH$_2$<br>\|      \\<br>        CH—<br>\|      /<br>CH$_2$—CH$_2$ | 276–278° C./74.6 | 298–300° C./91.5 | |
| CH$_2$—CH$_2$<br>\|      \\<br>        CH—CH$_2$—<br>\|      /<br>CH$_2$—CH$_2$ | | 262–264° C./79.0 | |

EXAMPLE 6

Ethyl 6,7-dihydroxy-4-methyl-2(1H)quinazolinone-1-propionate

A suspension of 6,7-dihydroxy-4-methyl-2(1H)quinazolinone-1-propionic acid (2.0 g, 6.5 mM) in absolute ethanol (35 ml) containing methanesulfonic acid (1.0 ml) is refluxed with stirring for 3 days. The reaction mixture is cooled to room temperature and quenched on ice (200 g). A yellow-green precipitate forms which is isolated, washed with water, acetone, and ether and then dried in vacuo to afford the product. (1.75 g, 92.2%); mp >308° C. (dec.); $\delta_{TMS}^{TFA}$ 1.35–1.60 (t, 3H, CH$_2$CH$_3$), 2.95–3.30 (m, 2H,

3.10 (s, 3H, CH$_3$), 4.20–4.60 (q, 2H, CH$_2$—O), 4.65–5.00 (t, 2H, CH$_2$—N), 7.35 (s, 1H, C$_5$—H), 7.75 (s, 1H, C$_8$—H); M+ 292.

EXAMPLE 7

6,7-Dihydroxy-3,4-dimethyl-3,4-dihydro-2(1H)quinazolinone-1-propionic acid

A solution of the quaternary salt 6,7-dihydroxy-3,4-dimethyl-2(1H)quinazolinonium-1-propionic acid bromide (1 meq) in glacial acetic acid (15 ml) is treated with 5% Pd/C (0.1 g) and the reaction mixture is hydrogenated at 45 psi for 12 hours. The catalyst is filtered and the mother liquor is poured into water (100 ml). The precipitate of 6,7-dihydroxy-3,4-dimethyl-3,4-dihydro-2(1H)quinazolinone-1-propionic acid is filtered, washed with water and dried in vacuo.

EXAMPLE 8

6,7-Dihydroxy-3,4-dihydro-4-methyl-2(1H)quinazolinone-1-propionic acid monohydrate A slurry of 6,7-dihydroxy-4-methyl-2(1H)quinazolinone-1-propionic acid monohydrate (5.0 g, 17.7 mM) in methanol (270 ml) is treated with Pd/C (10%, 2.5 g) and the mixture hydrogenated at 45 psi for 16 hours. Filtration, removal of the solvent in vacuo and titration of the residue with acetone gives the product as a tan solid (4.3 g, 91.4%); mp 202°–204° C.; $\delta_{TMS}^{TFA}$ 6.86 (s, 1H, 5—H), 6.83 (s, 1H, 8—H), 4.78 (d, 1H, J=7.0 Hz, 4—H), 4.36 (t, 2H, J=10 Hz, 2'—H), 3.03 (t, 2H, J=10 Hz, 1'—H), 1.55 (d, 3H, J=7 Hz, 4—CH$_3$); M+ 266.

EXAMPLE 9

6,7-Dihydroxy-3-benzyl-4-methyl-2(1H)quinazolinonium-1-propionic acid bromide

A solution of methyl 6,7-dimethoxy-4-methyl-2(1H)quinazolinone-1-propionate (10 g) in acetone (100 ml) is treated with benzyl bromide (10 eq) and the solution aged overnight at room temperature. The resulting crystalline precipitate is isolated and dried in vacuo.

The crude quaternary salt is then dissolved in a mixture of glacial acetic acid (70 ml) and 48% aqueous HBr (70 ml) and the reaction mixture refluxed with stirring for three days. Upon cooling to room temperature 6,7-dihydroxy-3-benzyl-4-methyl-2(1H)quinazolinonium-1-propionic acid bromide is isolated as a crystalline precipitate.

Identical conditions are utilized employing p-fluorobenzyl bromide and p-chlorobenzyl bromide to give the corresponding substituted benzyl quaternary salts.

EXAMPLE 10

6,7-Dihydroxy-4-norbornylmethyl-2(1H)quinazolinone-1-propionic acid hydrobromide A mixture of methyl 6,7-dimethoxy-4-norbornylmethyl-2(1H)quinazolinone-1-propionate (5 g), 48% aqueous HBr (40 ml) and glacial acetic acid (40 ml) is refluxed with stirring for three days. The solution is then cooled and the resulting gold precipitate isolated by filtration, washed with acetone (25 ml) and dried in vacuo to afford the title compound.

When in the above procedure methyl 6,7-dimethoxy-5-amino-4-methyl-2(1H)quinazolinone-1-propionate and methyl 6,7-dimethoxy-5-nitro-4-methyl-2(1H)quinazolinone-1-propionate are employed in place of methyl 6,7-dimethoxy-4-norbornylmethyl-2(1H)quinazolinone-1-propionate, the corresponding hydrobromides 6,7-dihydroxy-5-amino-4-methyl-2(1H)quinazolinone-1-propionic acid dihydrobromide and 6,7-dimethoxy-5-nitro-4-methyl-2(1H)quinazolinone-1-propionic acid hydrobromide are obtained. The propionate starting materials are prepared according to the procedure outlined in Example G.

EXAMPLE 11

6,7-Dihydroxy-4-methyl-2(1H)quinazolinone-1-propionic acid monopotassium salt A suspension of 6,7-dihydroxy-4-methyl-2(1H)quinazolinone-1-propionic acid (9.97 g, 37.10 mM) in methanol (30 ml) under nitrogen, is treated with 1N KOH in methanol (37.10 ml, 37.10 mM). The resulting yellow slurry is stirred at room temperature, under nitrogen, for 22 hours. The reaction mixture is cooled in an ice-water bath and filtered. The resulting yellow solid is washed with cold methanol (3×17 ml) and dried in vacuo at 120° C. for 336 hours (14 days). The product (10.41 g) is obtained as a yellow solid, mp=303°–305° C.

EXAMPLE 12

6,7-Dihydroxy-4-methyl-2(1H)quinazolinone-1-propionic acid dipotassium salt

A suspension of 6,7-dihydroxy-4-methyl-2(1H)quinazolinone-1-propionic acid (45.0 g 167.47 mM) in methanol (600 ml) is treated with 1N KOH in methanol (334.94 ml, 334.94 mM) at room temperature under nitrogen; a large amount of yellow solid is present after addition of the KOH. Additional methanol (200 ml) is added. Water is then added until the solid dissolves. The total amount of water added is 300 ml. The reaction mixture is then stirred at room temperature, under nitrogen for 30 minutes. The slightly cloudy solution is then filtered and concentrated to dryness in vacuo to give a yellowish-brown semi-solid. This is triturated with acetone (300 ml) and the resulting yellow solid filtered and dried to afford the dipotassium salt (54.26 g, mp >325° C.).

EXAMPLE 13

6,7-Dihydroxy-4-methyl-2(1H)quinazolinone-1-propionic acid monoarginine salt monohydrate A mixture of 6,7-dihydroxy-4-methyl-2(1H)quinazolinone-1-propionic acid (4.0 g, 14.6 mM) and L-arginine (2.34 g, 14.6 mM) in water (150 ml) is aged at room temperature for 3 hours. After 15 minutes the initial solution clears the then a yellow precipitate begins to form. After 3 hours, this precipitate is isolated, washed with water (15 ml), acetone (20 ml), and then ether (2×20 ml). The precipitate is dried in vacuo at 60° C. for 3 hours to give the amino acid salt (5.81 g, 93.8%).

EXAMPLE 14

6,7-Dihydroxy-4-methyl-2(1H)quinazolinone-1-propionic acid N-methylglucamine salt A mixture of 6,7-dihydroxy-4-methyl-2(1H)quinazolinone-1-propionic acid (0.79 g, 3 mM), meglumine (0.59 g, 3 mM), methanol (40 ml) and water (4 ml) is aged at ambient temperature overnight. The resulting slurry is filtered and the precipitate washed with ether (2×20 ml). After drying in air for 3 hours, the amine salt is isolated as a yellow solid, (0.88 g, 62.51%, mp=dec. 197°–8° C.).

The salts from monoethanolamine, piperazine, N-methylpiperazine and morpholine are prepared in a similar fashion.

EXAMPLE 15

6,7-Dihydroxy-4-methyl-2(1H)quinazolinone-1-propionic acid mono(2-methyl-2-amino-1,3-propandiol) salt monohydrate A suspension of 6,7-dihydroxy-4-methyl-2(1H)quinazolinone-1-propionic acid (1.0 g, 3.6 mM) in methanol (40 ml) and water (10 ml) is treated with mono(2-methyl-2-amino-1,3-propandiol) (0.38 g, 3.6 mM) and the mixture aged at ambient temperature for 16 hours. The resulting pale-yellow precipitate is isolated, washed with methanol (10 ml) and ether (2×10 ml). After drying in vacuo for 6 hours at 60° C., the amine salt (1.18 g, 85.5%) is isolated, mp=212°–13° C.

EXAMPLE 16

6,7-Dihydroxy-4-methyl-2(1H)quinazolinone-1-propionic acid mono(1-amino-2,3-propandiol) salt hemihydrate A mixture of 6,7-dihydroxy-4-methyl-2(1H)quinazolinone-1-propionic acid (0.84 g, 3 mM), mono (1-amino-2,3-propandiol) (0.27 g, 3 mM), methanol (40 ml) and water (10 ml) is aged overnight at room temperature. The resulting precipitate is isolated and washed with methanol (10 ml) and ether (1×20 ml). After drying under a stream of nitrogen for 3 hours, the amine salt (0.94 g, 84.7%) is obtained.

EXAMPLE 17

5,6-Dihydroxy-4-methyl-2(1H)quinazolinone-1-propionic acid Monohydroiodide

Methyl 5,6-dimethoxy-4-methyl-2(1H)quinazolinone-1-propionate (1.173 g, 3.83 mM) is treated with 50% aq HI (13 ml) at room temperature to give a clear orange solution which is refluxed under nitrogen for 11 hr. and then allowed to stir at room temperature overnight. The orange crystalline solid which precipitates is collected by filtration, washed with acetone and dried to give the product; yield 0.972 g, (65%), mp. 240°-241° C. (d) IR (KBr)μ, 3.23 (broad, OH), 5.78 (C=O).

When in the above procedure methyl 5,6-dimethoxy-4-trifluoromethyl-2(1H)quinazolinone-1-propionate, methyl 5,6-dimethoxy-4-isopropyl-2(1H)quinazolinone-1-propionate methyl 4-cyclopentyl-5,6-dimethoxy-2(1H)quinazolinone 1-propionate, and methyl 4-cyclohexylmethyl-5,6-dimethoxy-2(1H)quinazolinone-1-propionate are employed in place of methyl 5,6-dimethoxy-4-methyl-2(1H)quinazolinone-1-propionate the corresponding 5,6-dihydroxy-4-trifluoromethyl-2(1H)quinazolinone-1-propionic acid monohydroiodide, 5,6-dihydroxy-4-isopropyl-2(1H)quinazolinone-1-propionic acid monohydroiodide, 4-cyclopentyl-5,6-dihydroxy-2(1H)quinazolinone-1-propionic acid monohydroiodide and 4-cyclohexylmethyl-5,6-dihydroxy-2(1H)quinazolinone-1-propionic acid monohydroiodide are obtained. The ester starting materials are prepared according to the method outlined in Example G.

EXAMPLE 18

6,7-Dihydroxy-4-methyl-2(1H)quinozolinone-1-propionic acid Monohydrate

A suspension of methyl 6,7-dimethoxy-4-methyl-2(1H)quinazolinone-1-propionate (1.53 g, 5 mM), acetic acid (20 ml) and 48% aqueous HBr (15 ml) is refluxed for 120 hours under nitrogen. The solvent is removed in vacuo to yield a greenish hydrobromide salt (yield 1.5 g, 88.2%); mp 292°-295° C. A solution of the salt in methanol (5 ml) is treated with saturated aqueous NaHCO$_3$ until the pH is netural. The precipitated free base is collected by filtration and washed with acetone to obtain the product (yield 1.0 g, 76.9%) as a pale green solid, mp 308°-310° C.; NMR: $\delta_{TMS}^{TFA}$ 7.80 (s, 1H, 5—H), 7.46 (s, 1H, 8—H), 4.66-5.08 (m, 2H, 2'—H), 3.13 (m, 5H, 1'—H, 4—CH$_3$) M+264.

The various other substituted mono- and dihydroxy-2(1H)quinazolinones encompassed by the present invention can be prepared by any of the above methods using an appropriately substituted mono- or dialkoxy-2(1H)quinazolinone prepared according to the examples utilizing the various starting materials described below.

The biological activity of the novel quinazolinones was determined according to the method of Goldberg, L. I., Sonneville, P. F. and McNay, J. L. (1968). An investigation of the structural requirements for dopamine-like renal vasodilation; phenethylamines and apomorphine, *J. Pharmacol. Exp. Ther.* 163.

Adult mongrel dogs are anesthetized and surgically prepared for electromagnetic measurements of renal artery blood flow. A carotid artery is cannulated for measuring arterial blood pressure and drugs are administered intravenously. Heart rate is monitored by a cardiotachometer. Renal vascular resistance is calculated as the ratio of mean arterial blood pressure/renal artery blood flow. Dopamine is infused intravenously at 3 μg/min for ten minutes (1 ml/min) to determine responsiveness of each dog to renal dopamine receptor stimulation. Cumulative dose-response data are obtained by infusing the test drug at progressively increasing (usually three fold) infusion rates, each dose being infused five minutes. The maximum percent increase from pre-drug control in renal artery blood flow (or decrease in renal vasular resistance) is quantitated for each infusion dose.

PREPARATION OF STARTING MATERIALS

Example A 3,4-Dimethoxyphenylisocyanate

Phosgene (4 eq) is bubbled at a moderate rate into a 3-neck flask containing a solution of 3,4-dimethoxyaniline (1 eq.), in benzene (2 liters). The flask is cooled in an ice bath for 15 minutes and then the solution is refluxed for 1¾ hours while excess phosgene is added. The reaction mixture is then refluxed overnight and the solvent removed under vacuum. Acetone is added and the solvent is again removed under vacuum leaving a dark brown oily residue which is distilled at 132°-134° C./0.6 mm. Yield: 22.5 g.

Example B

N-(3,4-Dimethoxyphenyl)-N'-propionylurea

A mixture of 3,4-dimethoxyphenylisocyanate (26.0 g, 145 mM) and propionamide (10.61 g, 145 mM) is heated at 160°-165° C. for 1½ hours. A homogeneous pale yellow solution forms which after 15 minutes solidifies. The heating is discontinued and the flask is allowed to cool slowly. The mixture is triturated with acetone and this resulting white solid is filtered and dried. Yield: 32.45 g, mp 193°-197° C.

Example C 6,7-Dimethoxy-4-ethyl-2(1H)quinazolinone

A suspension of N-(3,4-dimethoxyphenyl)-N'-propionylurea (32.45 g, 128 mM) in polyphosphoric acid (375.12 g, 1109 mM) is heated at 130°-135° C. under nitrogen with vigorous stirring for 3.5 hours. The mixture is then poured onto 500 g ice-H$_2$O and stirred. The solution is brought to pH 5.5 with concentrated NH$_4$OH and allowed to stand at room temperature overnight. A brown precipitate forms. The resulting solid is filtered and dried to yield 7.40 g of a white solid. This filtrate is extracted with CHCl$_3$ (5×250 ml), the organic extract is dried (MgSO$_4$) and the solvent removed in vacuo to give a tan solid. The solid is triturated with acetone and filtered to give a tan solid (4.98 g). A sample is slurried in water and redried for additional purification, m.p. 263°-265° C. $\delta_{TMS}^{TFA}$ 7.50 (s, 1H, 5—H), 7.23 (s, 1H, 8—H), 4.30 (s, 3H, 6 or 7—OCH$_3$) 4.17 (s, 3H, 6 or 7—OCH$_3$), 3.50 (q, 2H, J=8.0 Hz, CH$_2$CH$_3$), 1.70 (t, 3H, J=8.0 Hz, CH$_2$CH$_3$).

Tabulated below are selected examples of 2(1H)quinazolinones prepared by the route described above.

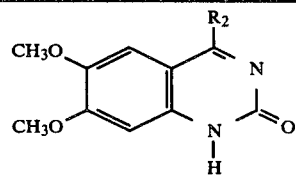

| R$_2$ | M.P./°C. | % Yield |
|---|---|---|
| H | 247-248 | 67.5 |
| CH$_3$ | 269-271 | 65.0 |
| CF$_3$ | 280-282 | 46.3 |
| propyl | 208-210 | 53.8 |
| isopropyl | 238-240 | 86.0 |

-continued

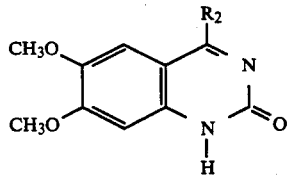

| R₂ | M.P./°C. | % Yield |
|---|---|---|
| n-pentyl | 152–154 | 21.9 |
| —CH₂—CH(CH₃)CH₃ | 199–202 | 14.4 |
| n-hexyl | 120–123 | 8.0 |
| n-heptyl | 184–186 | 78.2 |
| n-octyl | 130–132 | 24.4 |
| n-decyl | 166–167 | 37.4 |
| —CH₂-cyclobutyl | 262–264 | 79.0 |
| cyclobutyl-CH— (CH₂—CH₂, CH₂—CH—) | 253–255 | 12.6 |
| cyclopentyl-CH— | 196–197 | 37.0 |
| norbornyl-CH₂— | 298–302 | 16.6 |

Example D

3,4-Dimethoxy-6-nitroacetophenone 3,4-Dimethoxyacetophenone (1.8 eq) is added during 0.5 hour to nitric acid (18 eq), at 0°. After a further 1 hour at 20° C., the dark brown solution is poured onto ice water. The crude product is collected by filtration. Recrystallization from ethyl alcohol affords the purified product, mp=124°–126° C.; $\delta_{TMS}^{CDCl_3}$ 2.50 (s, 3H, CH₃), 4.00 (s, 6H, OCH₃'s), 6.80, 7.59 (2s, 1H ea., C₂H, C₅H).

Example E

6-Amino-3,4-dimethoxyacetophenone

A slurry of 1 equivalent of 3,4-dimethoxy-6-nitroacetophenone in methanol is treated with Pd/C (10%) and the mixture is hydrogenated at 45 psi for 24 hours. The residue after filtration and removal of solvent is crystallized from ethyl alcohol to afford purified product, mp=98°–100° C.; $\delta_{TMS}^{CDCl_3}$ 2.50 (s, 3H, CH₃), 3.80–3.85 (2s, 3H ea., OCH₃); 6.05, 7.05 (2s, 1H ea., C₂H, C₅H).

Example F

2-(N-Carbethoxyamino)-4,5-dimethoxyacetophenone

Ethyl chloroformate (1 eq) is added cautiously with stirring to 6-amino-3,4-dimethoxyacetophenone (0.3 eq) at room temperature. The dark brown reaction mixture is stirred at room temperature for ½ hour. Aqueous sodium hydroxide is added and the reaction mixture stirred at room temperature for an additional hour. The reaction mixture is extracted with chloroform. Removal of chloroform gives an oily residue. Recrystallization from ether affords the product, mp=97°–99° C.; $\delta_{TMS}^{CDCl_3}$ 1.10–1.50 (t, 3H, CH₃), 2.60 (s, 3H, CH₃), 3.85 and 3.95 (2s, 3H ea., OCH₃'s), 4.0–4.4 (q, 2H, CH₂), 7.15 and 8.20 (2s, 1H ea., C₂H, C₅H).

Example G

General Preparation of methyl 2(1H)quinazolinone-1-propionates

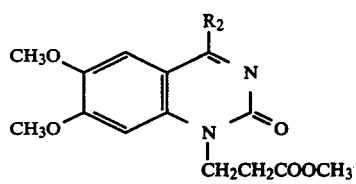

An appropriately substituted 2(1H)quinazolinone (5 g) is placed in a mixture of methanol (75 mol), chloroform (100 ml), methyl acrylate (125 ml) and excess Triton B (40% methanol) and the mixture is refluxed with stirring for 4–16 hours. The solution is then cooled and after evaporation of the solvent, the ester is obtained by chromatography on silica gel.

The following compounds are made by the above general procedure:

| R₂ | M.P./°C. |
|---|---|
| H | 186–188 |
| CH₃ | 155–157 |
| CF₃ | 140–143 |
| ethyl | 132–134 |
| propyl | 120–122 |
| isopropyl | 112–114 |
| n-pentyl | oil |
| n-hexyl | 122–124 |
| n-heptyl | 107–110 |
| n-octyl | 100–104 |
| n-decyl | oil |
| cyclobutyl-CH— | 140–142 |
| cyclopentyl-CH— | 103–105 |
| bicyclic-CH-CH₂— | 92–95 |

When in the above procedure 6-methoxy-4-methyl-2(1H)quinazolinone, 4-methyl-7-methoxy-2(1H)quinazolinone, 6-methoxy-2(1H)quinazolinone, 7-methoxy-2(1H)quinazolinone, 6-methoxy-4-trifluoromethyl-2(1H)quinazolinone and 7-methoxy-4-trifluoromethyl-2(1H)quinazolinone are employed as the starting materials, the corresponding 1-propionic acid esters are obtained.

When in the above procedure 3,4-dihydro-5,6-dimethoxy-4-methyl-2(1H)quinazolinone, 5,6-dimethoxy-4- methyl-2(1H)quinazolinone, 5,6-dimethoxy-4-trifluoromethyl-2(1H)-quinazolinone are employed as the substituted quinazolinone the corresponding 1-propionic acid esters are obtained.

Example H 6,7-Dimethoxy-4-methyl-2(1H)quinazolinone-1-(2-methanesulfonyl)ethane A solution of 6,7-dimethoxy-4-methyl-2(1H)quinazolinone (10 g) in chloroform (100 ml), methanol (100 ml) and methylvinyl sulfone (40 eq) is treated with Triton B (benzyltrimethylammonium hydroxide, 40% in methanol, 1.1 eq) and the solution refluxed, with stirring, for 24 hours. The solution is then cooled to room temperature and the solvent removed by concentration in vacuo. The residue is chromatographed on silica gel to afford purified 6,7-dimethoxy-4-methyl-2(1H)quinazolinone-1-(2-methanesulfonyl)ethane.

Example I 6,7-Dimethoxy-4-methyl-2(1H)quinazolinone-1-(2-benzoyl)ethane

A solution of 6,7-dimethoxy-6-methyl-2(1H)quinazolinone (10 g) in chloroform (100 ml), methanol (100 ml) and phenylvinyl ketone (40 eq) is treated with Triton B (40% in methanol, 1.1 eq) and the solution refluxed with stirring for 24 hours. After cooling to room temperature, the solvent is removed in vacuo and the residue chromatographed on silica gel. Purified 6,7-dimethoxy-4-methyl-2(1H)quinazolinone-1-(2-benzoyl)ethane is obtained.

Example J 6,7-Dimethoxy-4-methyl-2(1H)quinazolinone-1-[2-(2'-pyridyl)ethane]

A solution of 6,7-dimethoxy-4-methyl-2(1H)quinazolinone (10 g) in chloroform (100 ml), methanol (100 ml and 2-vinylpyridine (25 eq) is treated with Triton B (40% in methanol, 1.1 eq), and the solution refluxed with stirring for 24 hours. The resulting solution is cooled to room temperature and the solvent removed by concentration in vacuo. The residue is chromatographed on silica gel to give purified 6,7-dimethoxy-4-methyl-2(1H)quinazolinone-1-[2-(2'-pyridyl)ethane].

When in the above procedure 4-vinylpyridine is employed in place of 2-vinylpyridine the corresponding 4'-pyridyl derivative is obtained.

Example K 6,7-Dimethoxy-4-methyl-2(1H)quinazolinone-1-propionaldehyde

A solution of 6,7-dimethoxy-4-methyl-2(1H)quinazolinone (10 g) in methanol (100 ml), chloroform (100 ml) and acrolein (40 eq) is treated with Triton B (40% in methanol, 1.1 eq). The resulting mixture is concentrated in vacuo and the residue is chromatographed on silica gel to afford purified 6,7-dimethoxy-4-methyl-2(1H)quinazolinone-1-propionaldehyde.

Example L 6,7-Dimethoxy-4-methyl-2(1H)quinazolinone-1-propionitrile

A solution of 6,7-dimethoxy-4-methyl-2(1H)quinazolinone (10 g) in chloroform (100 ml), methanol (100 ml) and acrylonitrile (excess) is treated with Triton B (40% in methanol, x's). The solution is refluxed with stirring for 24 hours. The resulting solution is cooled to room temperature and the solvent is removed by evaporation in vacuo. The resulting residue is chromatographed on silica gel to give purified 6,7-dimethoxy-4-methyl-2(1H)quinazolinone-1-propionitrile.

Example M

Methyl 6,7-dimethoxy-4-methyl-2(1H)quinazolinone-1-(1-phenyl)propionate

A solution of 6,7-dimethoxy-4-methyl-2(1H)quinazolinone (10 g) in chloroform (100 ml), methanol (100 ml) and methyl α-phenylacrylate (excess) is treated with Triton B (40% in methanol, 1.1 eq) and the resulting solution refluxed with stirring for 24 hours. After cooling to room temperature, the solvent is removed in vacuo and the residue purified by chromatography on silica gel to give purified methyl 6,7-dimethoxy-4-methyl-2(1H)quinazolinone-1-(1-phenyl)propionate.

When in the above procedure methyl (2,4-difluorophenyl)acrylate, methyl (4-chlorophenyl)acrylate and methyl (4-methoxyphenyl acrylate are employed in place of methyl α-phenylacrylate, the corresponding quinazolinones methyl 6,7-dimethoxy-4-methyl-2(1H)quinazolinone-1-[1-(2,4-difluorophenyl)propionate]; methyl 6,7-dimethoxy-4-methyl-2(1H)quinazolinone-1-[1-(4-chlorophenyl)propionate]; and methyl 6,7-dimethoxy-4-methyl-2(1H)quinazolinone-1-[1-(4-methoxyphenyl)propionate] are obtained.

Example N

Methyl 6,7-dimethoxy-4-methyl-2(1H)quinazolinone-1-(2-phenyl propionate)

A solution of 6,7-dimethoxy-4-methyl-2(1H)quinazolinone (10 g) in chloroform (100 ml), methanol (100 ml), and methyl cinnamate (excess) is treated with Triton B (50% in methanol, 1.1 eq) and the resulting solution refluxed with stirring for 24 hours. The solution is concentrated in vacuo to remove the solvent and the residue is purified by chromatography on silica gel. In this manner, purified methyl 6,7-dimethoxy-4-methyl-2(1H)quinazolinone-1-(2-phenyl propionate) is obtained.

When in the above procedure methyl 2,4-difluorocinnamate, methyl 4-chlorocinnamate and methyl 4-methoxycinnamate are employed in place of methyl cinnamate, the corresponding quinazolinones methyl 6,7-dimethoxy-4-methyl-2(1H)quinazolinone-1-[2-(2,4-difluorophenyl)priopionate]; methyl 6,7-dimethoxy-4-methyl-2-(1H)quinazolinone-1-[2-(4-chlorophenyl)propionate] and methyl 6,7-dimethoxy-4-methyl-2(1H)quinazolinone-1-[2-(4-methoxyphenyl)priopionate] are obtained.

Example O 6,7-Dimethoxy-4-(2-norbornylmethyl)-2(1H)quinazolinone

A solution of norbornyl-2-acetic acid (25.0 g, 0.16 m) in benzene (50 ml) is treated with thionyl chloride (75 ml) and the mixture refluxed with stirring for 12 hours. The volatiles are removed on a rotary evaporator at about 50° C. The resulting acid chloride is dissolved in tetrahydrofuran (150 ml) and then aqueous concentrated ammonia (200 ml) is slowly introduced with stirring. A precipitate forms during the subsequent 30 minute aging period. It is isolated by filtration and washed well with cold water. After drying, 15.3 g (62.5%), mp=144°-6° C., of norbornyl-2-acetamide are obtained.

A mixture of 3,4-dimethoxyphenylisocyanate (8.95 g, 0.05 m) and norbornyl-2-acetamide (6.12 g, 0.04 m) is fused under nitrogen at 130°-140° C. with stirring for one hour. After cooling, acetone (100 ml) is introduced and the mixture broken-up manually. After one hour aging at room temperature, the precipitate is isolated and dried in vacuo. A solution of the adduct (9.0 g, 0.027 m) in polyphosphoric acid (200 g) is heated at 130°-140° C. for three hours with stirring. After cooling, the reaction mixture is quenched on ice (1500 g) and stirred well. This pale green solution is brought to pH~8.0 with concentrated ammonia. The resulting precipitate is isolated, washed with distilled water (2×50 ml) and dried to yield 6,7-dimethoxy-4-(2-norbornylmethyl)-2-(1H)quinazoline as a tan solid. After recrystallization from 95% ethanol, pale yellow crystals are obtained, 2.0 g, M.P. 231°-2° C.

Example P

Methyl 6,7-dimethoxy-4-methyl-2(1H)quinazolinone-1-(3'-methyl)propionate

Triton B (26.0 ml, 40% in methanol) is added as a slow stream with stirring to a solution of 6,7-dimethoxy-4-methyl-2(1H)quinazolinone (20.0 g, 91 mM) in methyl crotonate (90.0 g, 900 mM), methanol (80 ml), and chloroform (126 ml) precooled to 0° C. The reaction is stirred at reflux for 18 hours. The reaction mixture is then cooled to room temperature and the suspension is isolated by filtration. The filtrate is concentrated in vacuo to give a fluffy solid which is chromatographed on SilicAR CC-7 (125 g) prepared in 1:1 $CH_2Cl_2$/ethyl acetate. Elution with 5-20% methanol/$CH_2Cl_2$ affords the product as an orange solid (560 mg, 1.9%); mp 55°-56° C.

Example Q

Methyl 6,7-dimethoxy-4-methyl-2(1H)quinazolinone-1-(2'-methyl)propionate

Triton B (26.0 ml, 40% in methanol) is added as a slow stream with stirring to a solution of 6,7-dimethoxy-4-methyl-2(1H)quinazolinone (20.0 g, 91 mM) in methyl methacrylate (206 ml), methanol (79 ml), and chloroform (127.5 ml) precooled to 0° C. The reaction is stirred at room temperature for 18 hours and then heated at 50° C. for 66 hours. The suspension is cooled in an ice bath and the resulting precipitate is isolated by filtration. Water (75 ml) is added to the filtrate and this solution is extracted with methylene chloride (4×100 ml). The extract is dried (MgSO₄), filtered and concentrated in vacuo to give a reddish oil which is chromatographed on SilicAR CC-7 prepared in ethyl acetate. Elution with 5-10% ethyl acetate/ethanol gives an oil. Trituration of this oil with cold ethyl acetate/ether (1:1) deposits white crystals which are filtered, washed with ether (25 ml), and dried in vacuo to afford methyl 6,7-dimethoxy-4-methyl-2(1H)-quinazolinone-1-(2'-methyl)propionate.

Example R

Methyl 6,7-dimethoxy-4-norbornylmethyl-2(1H)quinazolinone-1-propionate

A solution of 6,7-dimethoxy-4-norbornylmethyl-2(1H)quinazolinone (10 g) in chloroform (50 ml), methanol (50 ml) and methylacrylate (50 ml) is treated with Triton B (benzyltrimethylammonium hydroxide, 40% in methanol, 20 ml, excess) and the reaction is refluxed with stirring for 24 hours. After work-up and purification via chromatography, the purified product is obtained.

Example S

Methyl 6,7-dimethoxy-3,4-dihydro-3,4-dimethyl-2(1H)quinazolinone-1-propionate

A solution of methyl 6,7-dimethoxy-3,4-dimethoxy-2(1H)quinazolinonium-1-propionate bromide (1 eq) in ethanol (700 ml) is treated with 10 g 10% Pd/C. The mixture is hydrogenated at ~45 psi for 16 hours until uptake ceases. The solution is filtered free of catalyst and the filtrate is concentrated in vacuo. The resulting solid is recrystallized from acetone to give a 60-70% yield of purified methyl-6,7-dimethoxy-3,4-dihydro-3,4-dimethyl-2(1H)quinazolinone-1-propionate.

Example T 6,7-Dimethoxy-5-nitro-4-methyl-2(1H)quinazolinone

One equivalent of 6,7-dimethoxy-4-methyl-2(1H)quinazolinone is added during ¾ hr. to a mixture (5:1) of 6 equivalents of concentrated nitric acid (70%) and concentrated $H_2SO_4$ at 0°±3° C. After one hour at the same temperature the solution is poured onto crushed ice (1000 ml). The crude product is collected by filtration, digested with boiling alcohol and the suspension is filtered. Crystallization from ethyl alcohol affords 6,7-dimethoxy-5-nitro-4-methyl-2(1H)quinazolinone.

Example U 6,7-Dimethoxy-5-amino-4-methyl-2(1H)quinazolinone

A solution of 13 equivalents of $FeSO_4.7H_2O$ in water (6 parts) is heated to 95° C. A slurry of 1 equivalent of 6,7-dimethoxy-5-nitro-4-methyl-2(1H)quinazolinone in water (800 ml) at 80° C. is added and the resulting yellow mixture is heated at 98°-100° C. for 15 minutes. Ammonium hydroxide (13 eq) is added to the mixture dropwise over a 15 minute period, maintaining the temperature at 98°-100° C. The resulting black reaction mixture is stirred at 98°-100° C. for 30 minutes, the hot mixture is filtered and the insoluble black residue is washed with hot water. The brownish filtrate is extracted with chloroform. The solvent is removed in vacuo to give a dark brown semisolid crude product, which is chromatographed on a silica gel column. Recrystallization of the crude product from ethyl alcohol affords purified product.

Example V 6,7-Dimethoxy-3,4-dimethyl-2(1H)quinazolinonium propionic acid methyl ester Iodide Hemihydrate A large excess of $CH_3I$ (20 ml) is added to a solution of methyl 6,7-dimethoxy-4-methyl-2(1H)quinazolinone propionate (2.0 g, 6.53 mM) in acetone (300 ml) and the mixture is refluxed for 3 days. Removal of the solvent in vacuo and subsequent trituration with ether yields a dark brownish solid (2.4 g). Crystallization from isopropyl alcohol and then from methanol affords the product as a yellow solid; yield 1.2 g (41.3%).

The starting materials for those compounds wherein the hydroxyl groups on the aromatic ring are in the 5-, 6- or 7-positions are prepared according to the following examples.

Example W

2-Hydroxy-3-methoxybenzaldehyde-2-benzenesulfonate

A slurry of 3-methoxysalicylaldehyde (45.6 g, 299 mM) in NaOH (138 ml, 15% aqueous solution) is treated with benzenesulfonyl chloride (66 g, 373 mM) and the mixture vigorously stirred for 1 hour. The reaction mixture is then poured into ice-water (500 ml) and the resulting white solid filtered, washed with cold water, and then recrystallized from acetic acid to afford the product as a white solid; yield 72.2 g (85%); m.p. 119°–120° C.

Example X

2-Hydroxy-3-methoxy-6-nitrobenzaldehyde-2-benzenesulfonate

2-Hydroxy-3-methoxybenzaldehyde-2-benzenesulfonate (50 g, 171 mM) is added to nitric acid (500 ml) at 0° C.–5° C. The solution is kept five minutes at 5° C. and then poured into ice-water (1.5 L). The crude product, a tan solid, is filtered, washed with cold water, alcohol, and then recrystallized from acetic acid (650 ml) to afford the product as a white solid; yield 30.3 g (52.6%); m.p. 152°–154° C.

Example Y

2-Hydroxy-3-methoxy-6-nitrobenzaldehyde

A slurry of 2-hydroxy-3-methoxy-6-nitrobenzaldehyde-2-benzenesulfonate (10.12 g, 30 mM) in methanol (120 ml) is heated to reflux. A solution of KOH (6 g) in water (24 ml) and methanol (12 ml) is added and the two phase mixture refluxed for 30 minutes. The light reddish precipitate which forms is filtered and then dissolved in boiling water (120 ml). Acidification of the hot aqueous solution with 10% aqueous HCl to pH~4 gives a yellow precipitate (5.0 g). Recrystallization from isopropyl alcohol affords the product as a yellow solid; yield 4.5 g (76.2%); m.p. 102°–104° C.

Example Z 2,3-Dimethoxy-6-nitrobenzaldehyde

A slurry of NaH (16.0 g, 50% oily dispersion, 337 mM) in dimethylformamide (200 ml) was treated dropwise with a solution of 2-hydroxy-3-methoxy-6-nitrobenzaldehyde (49.0 g, 248 mM) in DMF (300 ml) at such a rate that the temperature did not exceed 35° C. The mixture is aged at room temperature for 1 hour and then a large excess of methyl iodide (100 ml) is added dropwise. A slight exothermic reaction occurs. The mixture is then stirred vigorously for 19 hours at room temperature. After the removal of excess methyl iodide, the reaction mixture is poured into ice-water (1 l). The crude product, a brown solid, is filtered, washed with cold water, and then recrystallized from isopropyl alcohol (700 ml) to afford the product as a tan solid; yield 27.9 g (53.3%); m.p. 106°–108° C.

Example AA 2,3-Dimethoxy-6-nitrobenzaldehyde-ethyleneketal

A mixture of 2,3-dimethoxy-6-nitrobenzaldehyde (16.0 g, 75 mM), ethylene glycol (64 g, 103 mM), and p-toluenesulfonic acid monohydrate (0.2 g) in benzene (750 ml) is refluxed in a Dean-Stark apparatus for 48 hours. The solution is then poured into water (1 l.). The organic phase is washed with saturated aqueous NaHCO$_3$ (2×20 ml), dried over Na$_2$SO$_4$, filtered, and the solvent removed in vacuo. The crude product is recrystallized from n-hexane (2 l.); yield 15.2 g (78.2%); m.p. 74°–76° C.

Example BB

2-Amino-5,6-dimethoxybenzaldehyde ethyleneketal

A solution of 2,3-dimethoxy-6-nitrobenzaldehyde-ethyleneketal (12.1 g, 62.7 mM) in ethyl acetate (350 ml) containing sodium acetate (0.5 g) is treated with platinum oxide (1.0 g) and the mixture hydrogenated for 24 hours at ~50 psi. The solvent is removed in vacuo after filtering off the catalyst to give a pale brown oil. After crystallization from n-hexane, the product is obtained as a tan solid; yield 12.8 g (85.1%); m.p. 78°–80° C.

Example CC 2-(N-Carbethoxyamino)-5,6-dimethoxybenzaldehyde ethyleneketal

Ethylchloroformate (1.9 g, 17.5 mM) is added with stirring to 2-amino-5,6-dimethoxybenzaldehyde-ethyleneketal (1.6 g, 7.1 mM) dissolved in tetrahydrofuran (50 ml). A solution of sodium hydroxide in H$_2$O (0.72 g in 3.5 ml H$_2$O) is added and the resulting solution is stirred for 2 hours at room temperature. The tetrahydrofuran is removed in vacuo and the residue extracted with CHCl$_3$ (2×100 ml). The extracts are dried over Na$_2$SO$_4$, filtered, and the solvent removed in vacuo. The crude product is recrystallized from n-hexane; yield 1.2 g (57.1%); m.p. 95°–96° C.

Example DD 2-(N-Carbethoxyamino)-5,6-dimethoxybenzaldehyde 2-(N-Carbethoxyamino)-5,6-dimethoxybenzaldehyde-ethyleneketal (5.0 g, 16.8 mM) is dissolved in acetone (36 ml) and aqueous HCl (3 ml of 1N solution). The mixture is stirred at room temperature for 4 hours. The solvent is removed in vacuo to give a yellow solid (3.9 g). Recrystallization from n-hexane gives the pure product as a yellow solid; yield 3.6 g (84.7%); m.p. 86°–88° C.

Example EE 5,6-Dimethoxy-2(1H)-quinazolinone

A stream of dry ammonia gas is passed through a solution of 2-(N-carbethoxyamino)-5,6-dimethoxybenzaldehyde (12.4 g, 48.9 mM) and ammonium acetate (95 g) maintained at 155°–160° C. for 3 hours. The reaction mixture is cooled and poured into an ice-water mixture. A tan solid forms. The aqueous mixture is treated with NaCl (50 g) and then extracted with CHCl$_3$ (3×200 ml). The organic extracts are combined and the solvent is removed in vacuo to yield 9.2 g of a pale brown oil. Trituration of the oil with hot acetone gives the product as a yellow solid; yield 2.1 g (20.8%); m.p. 242°–244° C.

Example FF

3,4-Dihydro-5,6-dimethoxy-4-methyl-2(1H)quinazolinone

To a partial solution of 5,6-dimethoxy-2(1H)quinazolinone (10.0 g, 48.5 mM) in dry tetrahydrofuran (1100 ml) under nitrogen, is added at 0° C. over 20 minutes, an excess of methyl magnesium bromide in ether (62.60 ml of a 3.1M solution in ether, 194.06 mM). The reaction mixture is then removed from the cooling bath, allowed to reach room temperature and is stirred at room temperature for 16 hours. Additional methyl magnesium bromide is added (15.65 ml of a 3.1M solution in ether; 48.52 mM) and the reaction mixture is heated at reflux for 2 hours, cooled in an ice-water bath and an aqueous solution of NH$_4$Cl (100 ml of saturated NH$_4$Cl and 100 ml H$_2$O) is added with stirring. After the addition is complete, 10% aqueous HCl is added until a pH of ~6.0 is reached. The layers are separated and the aqueous layer is extracted with CHCl$_3$ (3×250 ml). The CHCl$_3$ extract is combined with the previously separated tetrahydrofuran layer, and the combined organic layers are washed with a saturated aqueous solution of NaCl (200 ml) and dried (Na$_2$SO$_4$). Filtration followed by concentration to ~250 ml affords an off-white precipitate which is filtered and recrystallized from isopropanol (200 ml) to give the product as a colorless solid; yield 9.7 g (87.8%), m.p. 210°-212° C.

Example GG

5,6-Dimethoxy-4-methyl-2(1H)quinazolinone

Potassium permanganate (25.6 g, 162.38 mM) is added to a solution of 3,4-dihydro-5,6-dimethoxy-4-methyl-2(1H)quinazolinone (18.04 g, 81.19 mM) in acetone (5.0 liters) and the mixture is stirred at room temperature (under nitrogen, protected from light with aluminum foil) for 96 hours. The brown precipitate which forms is filtered and washed with acetone (500 ml) and is partially dissolved in boiling water (1000 ml). The hot, aqueous solution (after filtration) is neutralized with 10% aqueous HCl and then extracted with CHCl$_3$ (4×250 ml) and 10% isopropyl alcohol/ethyl acetate (4×250 ml). The CHCl$_3$ extracts are dried (MgSO$_4$), filtered, and concentrated to 500 ml at which point a solid forms. The solid is filtered off and the filtrate is further concentrated in vacuo to give 3.25 g of a tan solid which is chromatographed on a 350 g SilicAR column that has been prepared in CHCl$_3$ (500 ml fractions). Elution with ½% methanol/chloroform affords a yellow solid (1.92 g) which upon recrystallization from isopropanol (75 ml) affords the product as a yellow solid; yield 0.940 g (5.3%); mp 230°-232° C.

When in the above procedure 3,4-dihydro-5,6-dimethoxy-4-trifluoromethyl-2(1H)quinazolinone, 3,4-dihydro-5,6-dimethoxy-4-isopropyl-2(1H)quinazolinone and 3,4-dihydro-4-cyclohexyl-5,6-dimethoxy-2(1H)quinazolinone are employed in place of 3,4-dihydro-5,6-dimethoxy-4-methyl-2(1H)quinazolinone the corresponding 5,6-dimethoxy-4-trifluoromethyl-2(1H)quinazolinone, 5,6-dimethoxy-4-isopropyl-2(1H)quinazolinone and 4-cyclohexyl-5,6-dimethoxy-2(1H)quinazolinone are obtained.

Example HH

2-(N-Carbethoxyamino)-5-methoxy-acetophenone

Ethyl chloroformate (8.6 g, .080 m) is added cautiously with stirring to 2-amino-5-methoxyacetophenone (8.0 g, 0.0479 m) while cooling the reaction mixture. A solution of sodium hydroxide in H$_2$O (3.2 g in 15 ml) is added slowly. The reaction becomes exothermic and all of the solids dissolve. The yellow reaction mixture is removed from the ice bath and allowed to stir at room temperature for 2 hours. The reaction mixture is then extracted with CHCl$_3$ (3×100 ml) dried over Na$_2$SO$_4$, filtered, and the solvent is removed in vacuo to give a yellow solid. Crystallization from hexane affords the product as a yellow solid; yield 7.4 g (65%); mp 90°-92° C.

Example II

6-Methoxy-4-methyl-2(1H)quinazolinone

A stream of dry ammonia gas is passed for 3 hours through a solution of 2-(N-carbethoxyamino)-5-methoxy-acetophenone (14.0 g, 0.058 m) and ammonium acetate maintained at 155°-160° C. The reaction mixture is cooled and poured into ice-water (750 ml) to give a dark orange solution. The solution is extracted with CH$_2$Cl$_2$ (3×500 ml) followed by ethyl acetate (2×500 ml) and n-butanol (2×500 ml); the combined organic extracts are dried over Na$_2$SO$_4$ and the solvent is removed to give a brownish residue. The residue is slurried in acetone and the insoluble portion is filtered to give the product as a pale yellow solid; yield 3.25 g, (25%); mp 232°-236° C. dec.

Example JJ

4-Methyl-7-methoxy-2(1H)quinazolinone

A mixture of 1-acetyl-3-(3-methoxyphenyl)urea (32.5 g, 0.156 m) and polyphosphoric acid (912.5 g) is heated at 120°-130° C. for 2 hours. After cooling to 50° C. the melt is poured on ice-water (2 liters), and the solution is made weakly basic with ammonia and left standing overnight. The brownish-red precipitate which forms is filtered off, washed with cold water followed by hot acetone, and crystallized from ethanol (after treatment with charcoal) to give the product as a pale yellow solid; yield 11.5 g (39.1%); mp 251°-254° C.

The 5,6-2(1H)quinazolinones having a substituent other than the methoxy group at C$_6$ and C$_7$ and a substituent other than lower alkyl at C$_4$ are prepared according to the methods described for the preparation of the corresponding 6,7-2(1H)quinazolinones.

What is claimed is:
1. A compound of the formula

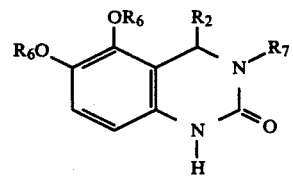

wherein R$_2$ is hydrogen, lower alkyl, cycloalkyl having 4-8 carbon atoms, cycloalkylalkyl wherein the cycloalkyl group has 4-8 carbon atoms and the alkyl group has 1-3 carbon atoms, haloalkyl having 1-3 halogen atoms and 1-4 carbon atoms, norbornyl and norbornylmethyl;

$R_6$ is lower alkyl and $R_7$ is hydrogen, provided that $R_7$ is hydrogen only when the 3,4-imine linkage is saturated.

2. A compound of claim 1 which is 5,6-dimethoxy-4-methyl-2(1H)quinazolinone.

3. A compound of claim 1 which is 3,4-dihydro-5,6-dimethoxy-4-methyl-2(1H)quinazolinone.

4. A compound of claim 1 which is 5,6-dimethoxy-2(1H)quinazolinone.

5. A pharmaceutical composition useful in the treatment of cardiovascular disorders in unit dosage form comprising from about 15 mg/kg to about 300 mg/kg of a compound of claim 1 in admixture with a pharmaceutically acceptable carrier.

6. The method of treating a patient having a cardiovascular disorder which comprises administering to said patient an effective amount of a compound of claim 1 in a pharmaceutically acceptable carrier.

* * * * *